(12) United States Patent
Kramer

(10) Patent No.: US 8,453,525 B2
(45) Date of Patent: Jun. 4, 2013

(54) PLASMA SAMPLE COLLECTION DEVICE

(75) Inventor: John P. Kramer, Aurora, IL (US)

(73) Assignee: HealthPoint Diagnostix, Inc., Lincolnshire, IL (US)

( * ) Notice: Subject to any disclaimer, the term of this patent is extended or adjusted under 35 U.S.C. 154(b) by 0 days.

(21) Appl. No.: 13/138,213

(22) PCT Filed: Feb. 9, 2010

(86) PCT No.: PCT/US2010/000393
§ 371 (c)(1),
(2), (4) Date: Jul. 20, 2011

(87) PCT Pub. No.: WO2010/090773
PCT Pub. Date: Aug. 12, 2010

(65) Prior Publication Data
US 2011/0283818 A1 Nov. 24, 2011

Related U.S. Application Data

(60) Provisional application No. 61/207,171, filed on Feb. 9, 2009.

(51) Int. Cl.
*G01N 1/22* (2006.01)
(52) U.S. Cl.
USPC ..................................... 73/863.21

(58) Field of Classification Search
None
See application file for complete search history.

(56) References Cited

U.S. PATENT DOCUMENTS

| | | | |
|---|---|---|---|
| 5,877,028 A * | 3/1999 | Chandler et al. | 436/514 |
| 8,062,608 B2 | 11/2011 | Pankow | |
| 2001/0039059 A1* | 11/2001 | Freitag et al. | 436/514 |
| 2008/0083618 A1* | 4/2008 | Neel et al. | 204/403.14 |
| 2008/0210644 A1* | 9/2008 | Milunic et al. | 210/767 |

* cited by examiner

*Primary Examiner* — Robert R Raevis
(74) *Attorney, Agent, or Firm* — Olson & Cepuritis, Ltd.

(57) ABSTRACT

A plasma sample collection device includes an elongated blood separation strip having a constant width and a relatively narrower end portion. A support base is located under the plasma separator strip and a cover is positioned superincumbent with respect to the blood separator strip. The cover defines an elongated observation window extending along the length of the plasma separator strip. An oblong collection port is adjacent to but spaced from one end of the observation window. The oblong collection port exposes the separator strip end portion and has a chief axis substantially aligned with the longitudinal axis of the blood separation strip. In one embodiment, the collection port has a teardrop configuration, and in another embodiment it has an obovate-cuneate configuration.

7 Claims, 4 Drawing Sheets

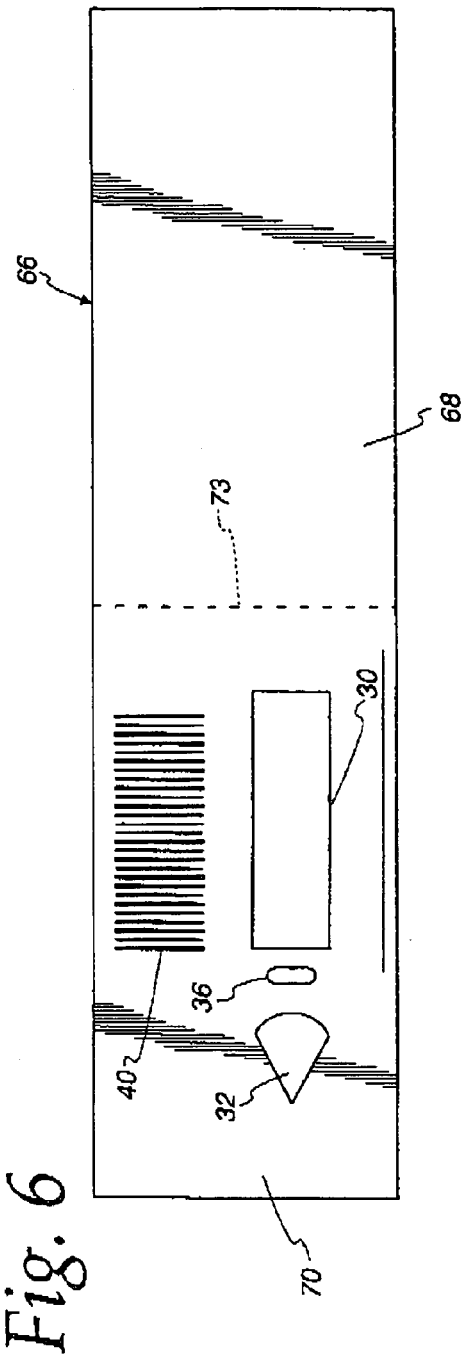
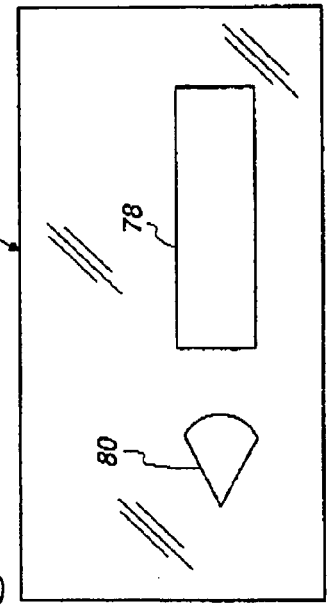
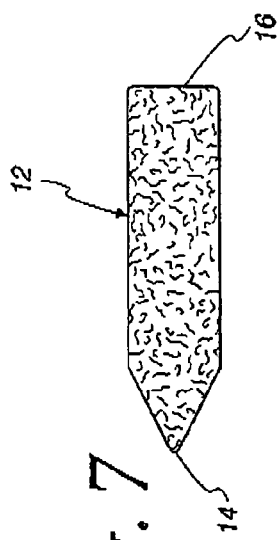

PLASMA SAMPLE COLLECTION DEVICE

CROSS-REFERENCE TO RELATED APPLICATIONS

The application is a U.S. National Stage of PCT/US2010/000393, filed Feb. 9, 2010, and claims benefit of U.S. Provisional Patent Application No. 61/207,171, filed Feb. 9, 2009, each of which is incorporated herein by reference in its entirety.

FIELD OF THE INVENTION

The present invention relates to devices for collecting plasma samples, and more particularly to such devices that obtain plasma samples from a whole blood aliquot.

BACKGROUND OF THE INVENTION

Improvements have been sought for methods of obtaining plasma samples that employ centrifuges and the like equipment used to separate plasma from whole blood and whole blood constituents or fractions such as red blood cells. Emphasis has been placed on the suitability of obtaining plasma samples that are suitable for rapid diagnostic assays used to measure a number of important physiologically active components of whole blood.

U.S. Published Patent Application No. 2008/0210644 describes a blood separator and a method utilizing a glass fiber and paper matrix for separating a fluid fraction from the whole blood. A device for collecting a whole blood sample and for separating a fraction such as plasma therefrom includes two rectangular shell-like pieces that are snapped together, to apply a particular physical stress to a blood separator composite. The device includes a collection port adjacent one end of the glass fiber composite and a second port spaced therefrom to provide access to a glass capillary to extract the fluid fraction separated from the whole blood.

U.S. Pat. No. 7,115,421 discloses a device for the visualization and measurement of hematocrit in a blood sample by separating blood plasma from red blood cells on an absorbent substrate provided with a blood plasma soluble dye.

U.S. Pat. No. 6,258,045 is directed to a collection device for biological samples. The device has a complicated construction and includes the use of capillary collection tubes that further add to the complexity of the device.

U.S. Pat. No. 4,816,224 discloses a device for separating plasma or serum from whole blood. The device includes a relatively complex arrangement, including various layers of glass fibers and the like to process the whole blood.

Despite these and other advances, a need still exists for improved sample collection devices.

SUMMARY OF THE INVENTION

The present invention provides a novel and improved blood collection device that minimizes the disadvantages associated with the prior art devices and provides advantages in construction, mode of operation and use. The collection device is useful for the recovery of plasma or serum samples from whole blood, rapidly separating a whole blood aliquot into its component fractions, providing a visual display of the separation process, and making the separated sample available for air drying so as to result in a physically stable condition suitable for transport to a remote location for analysis. The present collection devices are self contained and do not require use of external agents such as external equipment or external biologically active reagents or other materials.

A blood collection device or card embodying the present invention comprises an elongated blood separator strip having a substantially uniform width and a predetermined length, the separator strip terminating in a relatively narrower portion at one end thereof. Also included as part of the card is a support base for the blood separator strip and a cover superincumbent with respect to the blood separator strip. The cover defines an elongated observation window extending along the length of the blood separator strip and an oblong sample collection port that is adjacent to, but spaced from, one end of the observation window. The oblong collection port exposes the relatively narrower separator strip end portion, and has a principal or chief axis thereof substantially aligned with the longitudinal axis of the blood separator strip.

Preferably, the collection port of the blood sample collection device or card has a tear drop configuration, more preferably an obovate-cuneate configuration. A sight port defined by the cover is situated between the collection port and the observation window, and provides an indication that a sufficient quantity of whole blood has been collected by the device. Such indication can also be provided by a marker on the cover, and located adjacent the observation window a predefined distance from the relatively narrower end portion of the separator strip.

In other aspects of the present invention, a novel and improved cover blank for a blood sample collection device comprises a planar sheet defining an elongated observation window having a longitudinal axis and an oblong collection port adjacent to one end of the observation window, but spaced therefrom. The oblong collection port has a principal or chief axis substantially aligned with the longitudinal axis of the observation window.

The present invention also provides a method for recovering a plasma sample utilizing the aforementioned blood collection device or card. According to the method aspect, whole blood is deposited into the narrower end of the separator strip at the collection port. Whole blood collection continues until some of the whole blood migrates either to a sight port defined in the device and located between the collection port and the observation window, or until some of the whole blood migrates to a marker adjacent the observation window and situated at a predefined distance from the relatively narrower end portion of the blood separation strip. According to the method, the plasma migrates along the separator strip at a rate faster than red blood cells and provides a visually detectable separation result as well as a plasma or serum aliquot suitable for further analysis or diagnostic tests.

BRIEF DESCRIPTION OF THE DRAWINGS

The accompanying drawings illustrate preferred embodiments of the present invention.

In the drawings:

FIG. 6 is a schematic top plan view of a further embodiment of a cover component for a collection device illustrating other features of the present invention;

FIG. 7 is a schematic top plan view of one embodiment of a separator strip used in one or more of the collection devices;

FIG. 8 is a schematic top plan view of a blank for a cover component; and

DETAILED DESCRIPTION OF THE PREFERRED EMBODIMENTS

Figure 1:
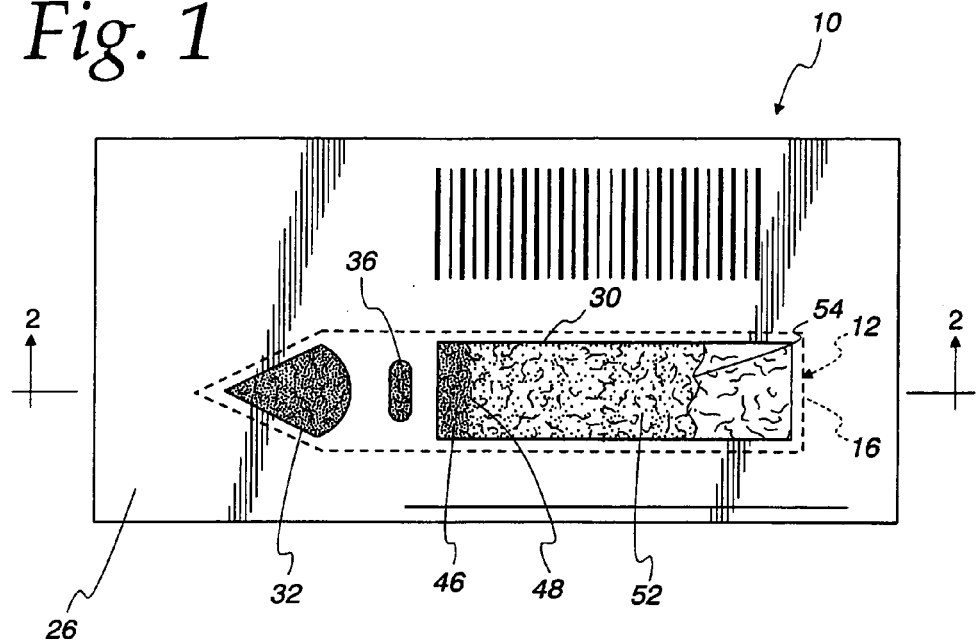
FIG. 1 is a schematic top plan view of one embodiment of a blood collection device or card according to certain aspects of the present invention.

The invention disclosed herein is, of course, susceptible of embodiment in many different forms. Shown in the drawings and described below in detail are preferred embodiments of the invention. It is understood, however, that the present disclosure is an exemplification of the principles of the invention and does not limit the invention to the illustrated embodiments.

For ease of description, collection devices and components for use therewith, which embody the present invention, are described herein below in their usual assembled positions as shown in the accompanying drawings, and terms such as upper, lower, horizontal, longitudinal, etc, may be used herein with reference to these usual positions. However, the collection devices and components thereof may be manufactured, transported, sold or used in orientations other than that described and shown herein.

Figure 2:
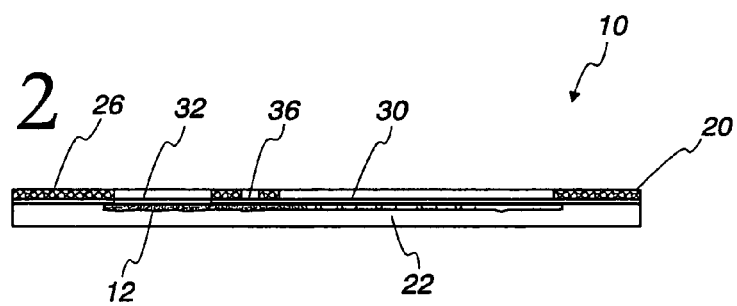
FIG. 2 is a cross-sectional view thereof taken along the plane 2-2 of FIG. 1.
Figure 3:
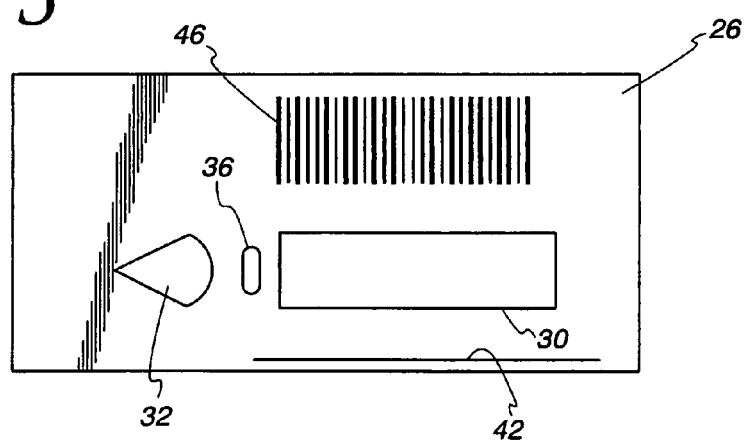
FIG. 3 is a schematic top plan view of a cover component of the device or card shown in FIG. 1.

Referring now to the drawings, and initially to FIGS. 1-2, a first embodiment of a blood sample collection device or card is generally indicated at 10. As will be seen herein, blood collection device 10, as is preferred for other blood collection devices described herein, is self contained and constructed so as to process a whole blood sample that is preferably obtained from a finger stick. The blood collection devices preferably contain one or more of the following features: an oblong collection port used to collect the blood sample, a separator strip to separate the blood sample into its components or fractions, and an observation window which provides a visual display of the separation process.

Plasma collection device 10 includes a blood separator strip generally indicated at 12 on a support base 22, which is hydrophobic and can be porous or non porous, as desired. Separator strip 12 is elongated and has a substantially uniform width substantially less than its longitudinal length. Separator strip 12 has a pair of opposed ends, including a relatively narrower end portion, preferably terminating in a point 14, and an opposed terminus end portion 16. As illustrated in FIG. 7, the narrower end portion is most preferably shaped in the form of a "V," but the narrower end portion may also take on a rounded, part rounded or polygonal shape.

The blood separator strip is a paper-like, hydrophobic strip made of a fibrous blood separation medium that separates plasma or serum from red blood cells in a lateral flow. The blood separator strip has a basis weight of about 40 to about 65 grams per square meter ($g/m^2$). A preferred material for the blood separator strip is a glass fiber paper composition commercially available from Whatman, Inc., Florham Park, N.J. 07932, U.S.A. under the designation LF1. For relatively higher flow capacities, sheet form blood separators having Whatman designations MF1, VF1 and VF2 can be utilized as well.

The separator strip length-to-width ratio can vary, but generally is in the range of about 3 to about 6. Preferably, the blood separator strip length-to-width ratio is in the range of about 4 to about 5.

The support base material can be conventional card stock that is water repellent. For rapid drying of a collected sample, the support base is made preferably of a hydrophobic porous material of construction such as a hydrophobic polyolefin sheet, e.g., a hydrophobic polyethylene sheet or a hydrophobic polypropylene sheet that may or may not include a dry surfactant in the pores thereof. For a porous, hydrophobic support base, an average pore size in the range of about 50 microns to about 175 microns, and a nominal sheet thickness of about 0.06 inches, are preferred. Particularly preferred are a hydrophobic, porous polyethylene sheet having an average pore size of about 90 to 130 microns and a hydrophobic, porous polypropylene sheet having a pore size of about 120 microns. Suitable such support base materials are commercially available from Interstate Specialty Products, 55 Gilmore Drive, Sutton, Mass. 01590, U.S.A. as Porex® sheets with the designations POR-4711, POR-4908 and POR-4913.

In use, whole blood is applied to separator strip 12 at/or adjacent the pointed end 14 and migrate components thereof at different rates toward terminus 16. During its migration toward the terminus 16, the whole blood is separated into fractions with red blood cells moving relatively slowly and plasma moving toward terminus 16 at a substantially faster rate. Preferably, separator strip 12 has a uniform thickness throughout and preferably has a substantially uniform composition.

Referring again to FIGS. 1 and 2, collection device 10 has a body 20 that includes a support base 22 under separator strip 12, so-called because it is generally preferred that the underlying support base 22 have a flat, planar or sheet-like configuration. As indicated in FIG. 2, underlying support base 22 is longer than the length of separator strip 12 and substantially encloses both ends 14, 16 of the separator strip. Cover 26 and underlying support base 22 can be separately formed and later joined together by sonic welding, snap-fit engagement or other conventional joinder means as is known in the art. Alternatively, the cover and the support can be unitary as will be discussed in detail hereinbelow.

Cover 26 defines a number of apertures, preferably up to three apertures, that are aligned along a common axis corresponding to the longitudinal axis of separator strip 12. Included among the apertures defined by cover 26 are an elongated observation window 30, and an oblong collection port 32, having an obovate-cuneate configuration, adjacent to, but spaced from, one end of observation window 30. As can be seen from the dashed lines of FIG. 1, separator strip 12 extends below both observation window 30 and collection port 32. Cover 26 also defines a third aperture, a sight port 36 located between observation window 30 and collection port 32. Cover 26 extends beyond all sides of separator strip 12 and is superincumbent with respect to the separator strip. Preferably, underlying support base 22 has dimensions similar to those of cover 26. Together, cover 26 and underlying support base 22 cooperate so as to surround and completely enclose separator strip 12.

Cover 26 further includes indicia 40, 42 appearing on the face of cover 26 to provide identifying information concerning the collection device, the patient, and the like. For example, as illustrated, indicia 40 may comprise a bar code printed or otherwise applied to the exposed surface of cover 26. Indicia 40 may be employed to identify, for example, the model of the collection device, the identity of the testing lab to which the device is to be sent for processing, the identity of the attending physician, the identity of the patient, or provide special instructions to personnel using, processing or otherwise coming in contact with the collection device. Indicia 42 provides a space for specialized information which may be hand written or otherwise applied to the collection device and provide information specific to that particular separation device, such as a patient's name or date of collection. If desired, other types of information, particularly information relevant to the processing of samples collected or the proper use or health precautions associated with the collection device may also be provided.

A sight port 36 is provided between collection port 32 and observation window 30. Whole blood, preferably obtained by a finger stick is collected at collection port 32 and deposited into separator strip 12 at or adjacent its narrower end portion 14. Upon contact with separator strip 12, different components of the whole blood migrate toward terminus 16 at different migration speeds. The relatively narrower end portion of separator strip 12 aids in the rate of migration of components of the blood sample toward terminus 16 as well as enhances plasma yield. The plasma trace appearing on the surface of separator strip 12 can be seen through observation window 30, which is provided so as to expose the upper surface of the separator strip, preferably throughout the major portion of its longitudinal extent. The observation window may be open to ambient surroundings or may be wholly or partly covered with a transparent pane of a plastic, glass or other material, that can be provided with perforations for facilitating air flow through the separator strip and thus accelerating drying of the collected sample.

Sight port 36, located between collection port 32 and observation window 30, tracks the migration of either whole blood or red blood cells as migration toward terminus 16 of the separator strip continues. Either whole blood or the red blood cell component thereof provides a ready visual indication by a red color inherent in either the whole blood or the red blood cells. These color values present a red color "flag" in sight port 36 when migration of either the whole blood or the red blood cells has reached the sight port. Via instructions preferably appearing in indicia on the face of cover 26, the bottom surface of underlying support 22, or by instructional material included with the collection device, an operator can be advised to stop collecting whole blood at collection port 32 when the red "flag" appears in sight port 36.

Indication of the "flag" at sight port 36 accomplishes two objectives. First, an adequate supply of whole blood is assured, as is necessary to present a sufficient amount of plasma along the visible length of separator strip 12 that is exposed by observation window 30. Second, gross overfilling of the collection port 32 with whole blood can be avoided.

The shading indicated in FIG. 1 as being visible through collection port 32, sight port 36, in an upstream portion 46 of the sight window, represents a red color value, indicating the presence of either whole blood or red blood cells. The practical interpretation of the color values appearing in FIG. 1 is that the color value visible through collection port 32 indicates that a sufficient amount of whole blood has been collected. The red color indication or band 46 appearing at the upstream end of separator strip 12 exposed by observation window 30, is a desired result of a limited intrusion of either red blood cells or whole blood that results after whole blood collection has ceased after the appearance of a color value in sight port 32. In FIG. 1, transition line 54 can be seen during the collection process and indicates the advancing movement of the plasma toward terminus 16.

Figure 4:
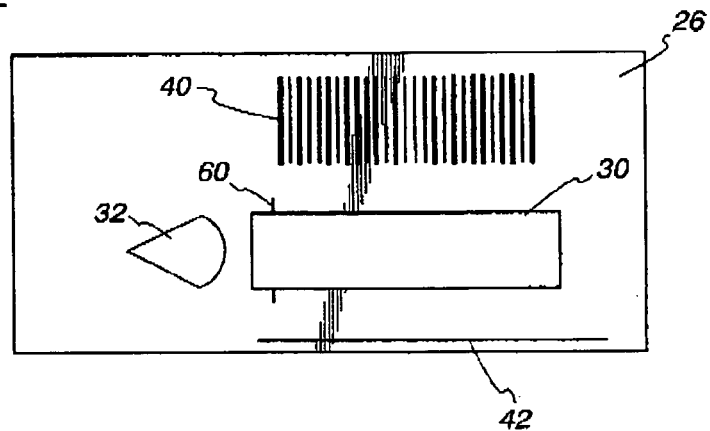
FIG. 4 is a schematic top plan view of an embodiment of a cover component for the collection device or card.

With reference to FIG. 4, an alternative embodiment of cover 26 includes a marker 60 in place of the aforedescribed sight port 36. Marker 60 provides indication to an operator that upon migration of whole blood or red blood cells to the indicated marker line, further blood collection should be stopped.

Figure 5:
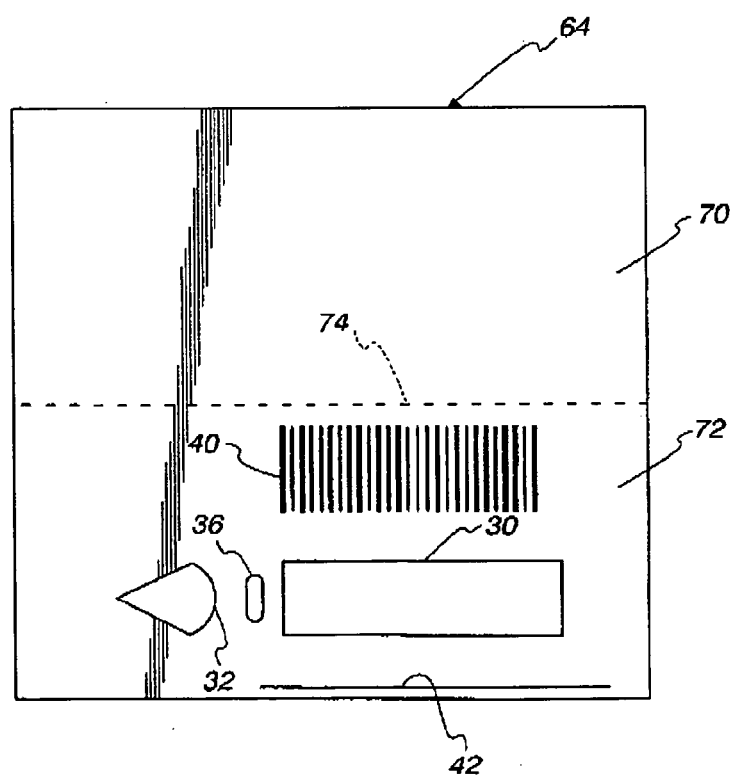
FIG. 5 is a schematic view of yet another embodiment of a blood collection device illustrating certain features of the present invention.

Referring now to FIGS. 5 and 6, further embodiments of plasma collection devices 64, 66 are shown. Both plasma collection devices 64, 66 include a support base unitary with the cover. For example, referring to FIG. 5, collection device 64 has an underlying support base 70 and a cover 72 delineated from one another by a fold line 74. As in the preceding embodiment, separator strip 12 has the same general shape and features as those described above as do the apertures 30, 32 and 36 formed in cover 72.

Referring now to FIG. 6, the construction of collection device 66 is similar to that described above with respect to collection device 64 shown in FIG. 5. In collection device 66, the body is also made from a single blank of card stock material and includes underlying support base 68 and cover 70 separated by fold line 73.

A more preferred configuration of the separator strip is illustrated in FIG. 7. Separator strip 12 has one relatively narrower end portion having a triangular configuration that terminates in a point 14 and an opposite, squared off end portion 16. The included angle in the triangular end portion that serves as the end portion receiving the drops of blood preferably is about 50 degrees.

Referring now to FIG. 8, a cover blank is generally indicated at 76. Cover blank 76 is preferably made of card stock or other sheet material and may be attached to other components such as an underlying support of the same or different material, such as plastic, metal or the like. Cover blank 76 includes apertures 78, 80 which function as an observation window and a collection port, respectively. The cover blank 76 may also be dimensioned to provide the cover/support base combination of FIG. 5 or FIG. 6. A sight port such as the sight port 36 described above may also be incorporated into the cover blank 76.

As described in the various preferred embodiments herein, a separator strip is provided between an underlying support and a superincumbent or overlying cover. If desired, the separator strip may be secured at its edges to either the underlying support and/or the cover with which it is associated. Alternatively, the bottom surface of the separator strip may be adhered to the underlying support layer using conventional means such as adhesives. As a further alternative, the underlying support and superincumbent cover may be joined together in such a way as to hold the separator strip in fixed position with respect to the various openings and ports formed in the cover. Further, an encapsulating body that provides the apertured cover and the support card may surround the separator strip.

As mentioned above, the various embodiments of collection devices and covers are provided with an oblong collection port, having a chief axis aligned along the longitudinal axis of the separator strip. The oblong collection port, as mentioned, exposes a portion of the separator strip. Preferably, the narrower end portion of the separator strip is configured to terminate at a point or other variously shaped portion of reduced width, compared to the preferred generally constant width of the major elongated body portion of the separator strip. According to one aspect of the present invention, the collection port is made to have a defined shape found, together with the contoured end portion of the separator strip, to enhance the separation process. If desired, the oblong collection port may have a tear drop configuration, but most preferably has an obovate-cuneate configuration.

Figure 9:
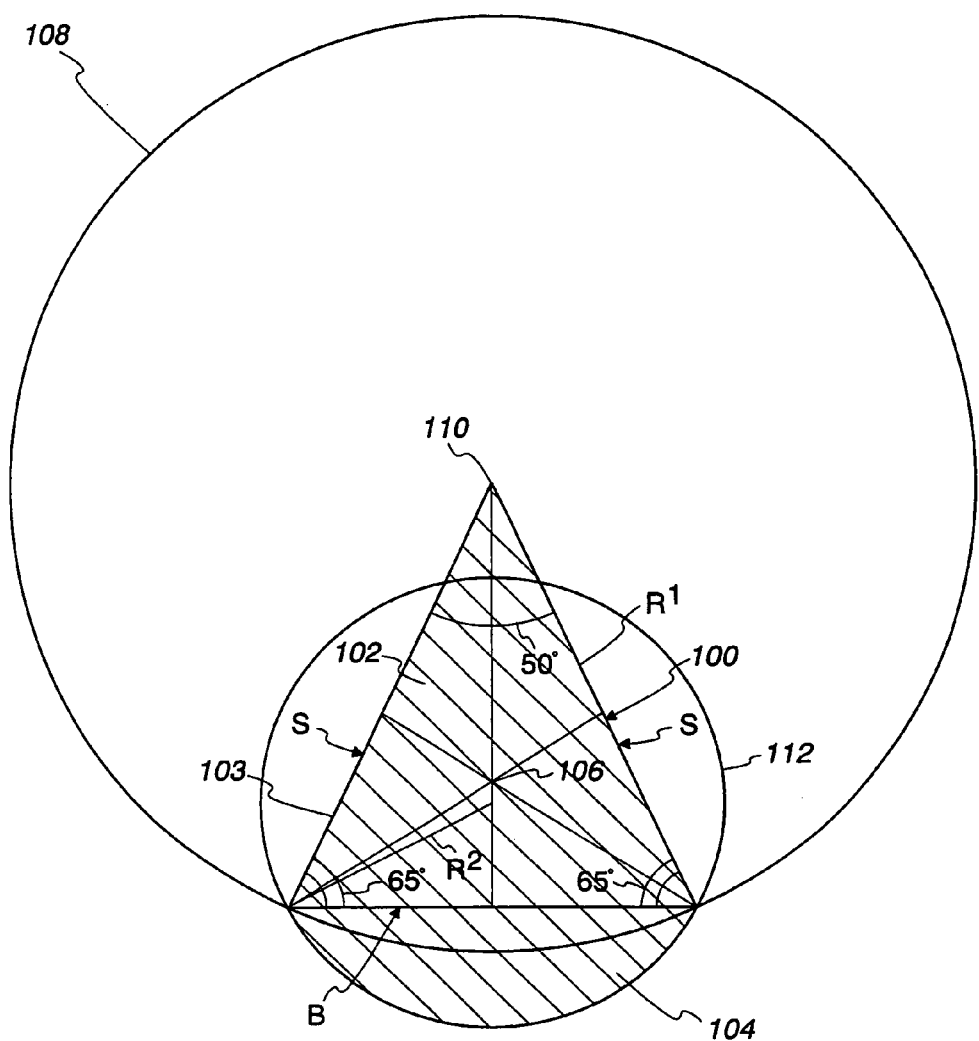
FIG. 9 is a schematic diagram illustrating one technique for forming an obovate-cuneate collection port for a device or card embodying the present invention.

Generation of preferred obovate-cuneate configurations for the collection port is illustrated in FIG. 9. As will be seen herein, the present invention contemplates a set or family of obovate-cuneate configurations for the collection port. These configurations are related to a range of mathematical values that are bounded by maximum and minimum limits, as will be explained herein. Cuneate portion 102 and obovate portion 104 together define the configuration of the aperture for the collection port 100. In FIG. 9, a single configuration of the family of configurations is shown for illustrative purposes, since the present invention is not limited to the particular configuration illustrated in FIG. 9. Cuneate portion 102 has the outline of an isosceles triangle 103 with an apex vertex 110 defining an included angle of about 50° equal sides S and base B. Preferably, the angle included is in the range of about 30° to about 80°, more preferably about 50 degrees.

Centroid 106 is the geometric center of the isosceles triangle and is the point of intersection of the triangle medians, i.e., the lines joining each vertex of the triangle 103 with the midpoint of the opposite side. Centroid 106, by the preferred definition contemplated herein, divides each of resulting medians in a 2:1 ratio. Accordingly, with regard to the vertical median line extending through the centroid, centroid 106 is located one-third of the perpendicular distance along the vertical median line from the base of triangle 103 to its apex vertex 110. A circle 108 having a radius $R^1$ equal to one of the sides of triangle 103 and circumscribed about triangle 103 represents one boundary of an obovate portion 104 of the obovate-cuneate configuration 100.

The size and shape of the obovate portion 104 can be selected as desired by scribing a circle 112 of radius $R^2$ over triangle 103 so that $R^1 \geq R^2 \geq B/2$ and the center of the circle with radius $R^2$ being situated on the vertical median line extending from base B to apex vertex 110. Accordingly, the obovate portion 104 can be varied by varying radius $R^2$ within the limits set out herein, that is, between a minimum inclusive limit of $R^2=B/2$ and a maximum inclusive limit of $R^2=R^1$. Changing the value of $R^2$ will of course change the shape of the obovate portion of the obovate-cuneate configuration. According to certain aspects of the present invention, collection ports having any of these defined obovate-cuneate characterisitics and positioned over separator strips having the above described narrower end portions and relatively constant width major body portions are found to enhance a rapid and reliable separation of the components of the whole blood collected.

As mentioned above, the windows formed in the covers of the collection devices preferably expose the major portion of the separator strip where separation is made to occur. Thus, personnel have ready visual access to the separation process as it occurs, and afterwards to verify that the separation process results are as intended. Further, the exposed portion of the separator strip is made available for subsequent analytical or diagnostic testing to be carried out at a later time and/or at a remote location. If further protection of the acquired plasma sample is desired, the observation window may be filled either partly or entirely, by a pane of transparent material such as glass, plastic or the like, solid or perforated, to promote drying of the collected sample, if desired. Alternatively, the pane can be permanently installed, requiring analytical lab personnel to separate the cover from the remaining portion of the collection device in order to gain access to the plasma trace appearing on the separator strip. The transparent pane also may be made removable so as to give analytical laboratory personnel the ability to access the plasma trace without requiring further disassembly of the collection device.

The present invention is illustrated by the following examples.

EXAMPLE 1

Serum Migration Rate in Card with Open Window and Nonporous Support Base

Blood separator strips were cut from Whatman LF1 blood separator sheet to produce a pointed end portion having different included angles and mounted into a card of the type shown in FIGS. 1 and 2. The support base for the separator strips was nonporous polyethylene sheet. The cover for the blood separator strips defined an open observation window.

Sets of 20 cards each were prepared for included angles of 180 degrees (square cut), 88 degrees, 52 degrees, 32 degrees and 20 degrees.

Medium large drops of blood (about 150 microliters, 4-5 drops) were applied through the collection port of each card to the blood separator strip at 25 millimeters from the relatively narrower end of the separator strip at a relative humidity of 21 percent and at an ambient temperature of about 24° C. The cards were maintained in a horizontal position at all times, and serum migration along the blood separator strip was observed and timed. The observed results were averaged for each 20-strip set and are reported in Table 1 below.

TABLE 1

| Serum Migration Rate Included Angle, Degrees | | | | | | | | | | | | | | |
|---|---|---|---|---|---|---|---|---|---|---|---|---|---|---|
| 180 | | | 88 | | | 52 | | | 32 | | | 20 | | |
| TMC | DT | USE | TMC | DT | USE | TMC | DT | USE | TMC | DT | USE | TMC | DT | USE |
| 240 | 26 | 12 | 231 | 30 | 15 | 210 | 35 | 17 | 216 | 28 | 16 | ERR | ERR | 10-12 |

TMC - average time to completion of migration, seconds
DT - average distance traveled by red blood cells, millimeters
USE - average usable serum extracted, length of strip in millimeters
ERR - erratic results, meaningful average not calculated The foregoing results indicate that a relatively narrower end portion of the blood separator strip at the blood sample receiving end in a card embodying the present invention reduces the average time to completion for the serum migration and also results in more usable serum amount that is available for subsequent analysis.

EXAMPLE 2

Effect of Porous Support Base on Serum Migration Rate

A set of 20 cards was prepared as described in Example 1 above, except that a porous polyethylene support base (POREX® POR-4913) was utilized and the observation window was covered by a transparent sheet. The included angle at the relatively narrower end for the separator strip was 52 degrees.

Medium large drops of blood (about 150 microliters, 4-5 drops) were applied through the collection port of each card to each blood separator strip at 25 millimeters from the relatively narrower end of the separator strip at a relative humidity of 21 percent and at an ambient temperature of about 24° C. The cards were maintained in a horizontal position at all times, and serum migration along the blood separator strip was observed and timed. The observed results were averaged for the set of 20 cards and are compiled in Table 2 below.

TABLE 2

| Serum Migration Rate Included Angle, 52 Degrees | | |
|---|---|---|
| TMC | DT | USE |
| 210 | 31 | 22 |

The foregoing results, and the comparison thereof with the results shown in Table 2 above, indicate that a porous support base for the blood separator strip in a card embodying the present invention enhances the average yield of extracted usable serum amount without an adverse effect on the average time to completion of migration.

The foregoing descriptions and the accompanying drawings are illustrative of the present invention. Still other variations and arrangements of parts are possible without departing from the spirit and scope of the invention. Further, the invention consists of certain novel features and a combination of parts herein fully described, illustrated in the accompanying drawings, and particularly pointed out in the appended claims, it being understood that various changes in the details may be made to one or more of these features without departing from the spirit or sacrificing any of the advantages of the present invention.

What is claimed is:

1. A blood sample collection device which comprises:
   an elongated blood separator strip having a substantially uniform width and a predetermined length, the separator strip terminating in a relatively narrower end portion at one end thereof;
   a support base under the blood separator strip; and
   a cover superincumbent with respect to the blood separator strip;
   the cover defining an elongated observation window extending along the length of the blood separator strip and an oblong collection port adjacent to but spaced from one end of the observation window, the oblong collection port exposing the relatively narrower end portion of the separator strip and having a chief axis thereof substantially aligned with a longitudinal axis of the blood separation strip.

2. The blood sample collection device in accordance with claim 1 wherein the collection port has a tear drop configuration.

3. The blood sample collection device in accordance with claim 1 wherein the collection port has an obovate-cuneate configuration.

4. The blood sample collection device in accordance with claim 1 wherein a sight port is defined by the cover between the collection port and the observation port.

5. The blood sample collection device in accordance with claim 1 wherein the observation window has a transparent pane.

6. The blood sample collection device in accordance with claim 1 wherein the relatively narrow end portion terminates in a point and has an included angle in the range of about 30 degrees to about 80 degrees.

7. The blood sample collection device in accordance with claim 1 wherein the relatively narrow end portion is triangular, terminates in a point, and has an included angle of about 50 degrees.

\* \* \* \* \*